(12) United States Patent
Steiner et al.

(10) Patent No.: US 8,173,681 B2
(45) Date of Patent: May 8, 2012

(54) METHOD FOR THE PROTECTION OF MATERIALS

(75) Inventors: Johann Steiner, Basel (CH); Amber Paula Marcella Thys, Beerse (BE); Mark Arthur Josepha Van Der Flaas, Beerse (BE)

(73) Assignee: Syngenta Corp. Protection, Greensboro, NC (US)

( * ) Notice: Subject to any disclaimer, the term of this patent is extended or adjusted under 35 U.S.C. 154(b) by 1078 days.

(21) Appl. No.: 10/580,583

(22) PCT Filed: Nov. 25, 2004

(86) PCT No.: PCT/EP2004/013392
§ 371 (c)(1),
(2), (4) Date: Aug. 19, 2008

(87) PCT Pub. No.: WO2005/051081
PCT Pub. Date: Jun. 9, 2005

(65) Prior Publication Data
US 2008/0306119 A1    Dec. 11, 2008

Related U.S. Application Data

(60) Provisional application No. 60/525,602, filed on Nov. 26, 2003.

(51) Int. Cl.
*A01N 43/40* (2006.01)
*A01N 43/653* (2006.01)
*B32B 21/04* (2006.01)
*A01P 15/00* (2006.01)
*B05D 1/02* (2006.01)
*B05D 1/12* (2006.01)
*B05D 1/18* (2006.01)
*B05D 1/28* (2006.01)
*C23C 16/44* (2006.01)

(52) U.S. Cl. ............... 514/341; 514/383; 428/537.1; 427/427.1; 427/254; 427/180; 427/440; 427/427

(58) Field of Classification Search ............. None
See application file for complete search history.

(56) References Cited

U.S. PATENT DOCUMENTS

| 5,250,556 A | 10/1993 | Steck et al. |
| 5,874,456 A | 2/1999 | McDade |
| 5,985,903 A * | 11/1999 | Assmann et al. ........... 514/359 |
| 2001/0046946 A1 | 11/2001 | Unhoch et al. |
| 2004/0044040 A1 * | 3/2004 | Neubert et al. ........... 514/332 |

FOREIGN PATENT DOCUMENTS

| WO | 9722254 | 6/1997 |
| WO | 9857543 | 12/1998 |
| WO | 0028825 | 5/2000 |

OTHER PUBLICATIONS

Hanson et al. (Mycology Research. (Mar. 2002); 106 (3): 321-328).*

* cited by examiner

*Primary Examiner* — Shanon A Foley
(74) *Attorney, Agent, or Firm* — Williams A. Teoli, Jr.

(57) ABSTRACT

The present invention relates to the use of the compound A) 4-(2,2-difluoro-1,3-benzodioxol-4-yl)pyrrole-3-carbonitrile (fludioxonil) as a microbicide for the protection of engineering or industrial materials, to mixtures containing such compound, and to the use of such mixtures for the protection of engineering or industrial materials.

20 Claims, No Drawings

METHOD FOR THE PROTECTION OF MATERIALS

This application is a 371 of International Application No. PCT/EP2004/013392 filed Nov. 25, 2004, which claims priority to U.S. 60/525,602 filed Nov. 26, 2003, the contents of which are incorporated herein by reference.

The present invention relates to compositions and methods for the protection of engineering or industrial materials. In particular, the invention relates to the use of phenylpyrrole derivatives as microbicides for the protection of engineering or industrial materials.

More particularly, the present invention relates to the use of the compound A) 4-(2,2-difluoro-1,3-benzodioxol-4-yl)pyrrole-3-carbonitrile (fludioxonil) as a microbicide for the protection of engineering or industrial materials, to novel mixtures containing such compound, and to the use of such mixtures for the protection of engineering or industrial materials.

The compound A), fludioxonil, is represented by the formula (I)

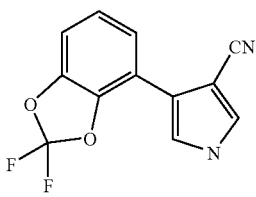

This compound, its synthesis as well as is antimicrobial properties are described in U.S. Pat. No. 4,705,800, which is incorporated herein by reference.

Mixtures of fludioxonil and tebuconazole and their use to protect materials of animal or vegetable origin against attack by plant pathogenic fungi are disclosed in U.S. Pat. No. 5,250,556. Similarly, mixtures of fludioxonil and difenoconazole and their use to protect materials of animal or vegetable origin against attack by plant pathogenic fungi are disclosed in U.S. Pat. No. 5,250,557. Mixtures of fludioxonil and triticonazole or cyproconazole and their use to protect plants and plant propagation material such as seeds and plant cuttings against disease infestation are disclosed in EP 0 993 247. Mixtures of fludioxonil and prothioconazole and their use to combat pathogenic fungi by application to plants, seed, ground, areas, materials or spaces are disclosed in WO 03/090538. Wood preserving agents comprising fludioxonil are disclosed in EP 1 025 967, JP 2003/160402 and JP 2002/326207.

In one embodiment, the present invention relates to a method of controlling microbial growth on or in engineering material, which comprises applying an antimicrobially effective amount of an antimicrobial composition that comprises A) fludioxonil to the engineering material to be treated.

As used herein, the following terms have the designated definitions, unless the context clearly indicates otherwise. The terms "microbicide", "microbicidal" and "antimicrobial" refer to a compound capable of inhibiting the growth of or controlling the growth of microorganisms at a locus; microbicides include bactericides, fungicides and algaecides. The term "microorganism" includes, for example, fungi, yeast, bacteria and algae.

"Engineering material" or product according to the invention include, for example, non-live materials (other than natural substances of plant or animal origin such as leather or wood) which have been prepared for use in engineering. For example, engineering materials which are intended to be protected by the active compounds from microbial growth which leads to change or destruction of the material can be glues, sizes, paints and plastic articles, cooling lubricants, aqueous hydraulic fluids and other non-live materials which can be infested with, or decomposed by, microorganisms. Parts of production plants, for example cooling-water circuits, which may be impaired by the multiplication of microorganisms may also be mentioned from amongst the materials to be protected.

In one embodiment, the present invention relates to a method of controlling microbial growth on or in engineering material, which comprises applying an antimicrobially effective amount of an antimicrobial composition that comprises A) fludioxonil to the engineering material to be treated, wherein the antimicrobial composition further comprises at least one compound B) selected from the group consisting of: azaconazole, bitertanol, bromuconazole, cyproconazole, diclobutrazol, difenoconazole, diniconazole, diniconazole-m, epoxiconazole, etaconazole, fenbuconazole, fluquinconazole, flusilazole, flutriafol, furconazole, furconazole-cis, hexaconazole, imibenconazole, ipconazole, metconazole, myclobutanil, oxpoconazole fumarate, paclobutrazol, pefurazoate, penconazole, propiconazole, prothioconazole, quinconazole, simeconazole, tebuconazole, tetraconazole, triadimefon, triadimenol, triticonazole, uniconazole, and uniconazole-p.

The active compound A) fludioxonil is mixed with at least one other antimicrobially active substance B) to increase the spectrum of action or to achieve particular effects such as, for example, allowing the application rate of the fungicides to be reduced while still maintaining an equally good fungicidal activity, or that identical application rates of the fungicides result in a greater activity than the activity to be expected from the individually employed active substances. Such mixtures can provide a synergistic effect, that is to say, the activity of the mixture is greater than the activity of the individual components.

The antimicrobially active compounds, when appropriate, may be independently used in the compositions or methods of the invention as stereochemical mixtures or stereochemical isomers.

In addition, the antimicrobially active compounds may be independently employed in the compositions or methods of the invention in free form or, if appropriate, in salt form. Suitable salt forms include addition salts, metal complexes and solvates.

Mixtures of the active compounds A) and B) are employed in the compositions and methods according to the present invention such that a suitable antimicrobial effect is obtained upon application. In particular, it is contemplated that in the compositions to be used directly, the concentration of A) fludioxonil taken as base equivalent, may range from 10 to 15000 ppm, in particular from 50 to 12000 ppm or from 50 to 6000 ppm, more in particular from 100 to 3000 ppm; and the concentration of compound B) taken as base equivalent is contemplated to range from 10 to 15000 ppm, in particular from 50 to 10000 ppm or from 100 to 8000 ppm, more in particular from 200 to 6000 ppm. In many instances said compositions to be used directly can be obtained from concentrates upon dilution with aqueous or organic media, such concentrates also being intended to be covered by the term composition as used in the definitions of the present invention. The content of the active compounds in the above-indicated compositions is from 0.01 to 95%, preferably from 0.1 to 50% more preferably from 0.1 to 20% and in particular from 0.2 to 15% by weight. The compositions according to the invention are preferably used in the form of solutions, suspensions or microemulsions.

The ratio A):B) between the active compounds A) and B) in said compositions may vary within relatively broad ranges and will be dependent on the application aimed at. However, for practical reasons, a quantitative ratio such that a suitable antimicrobial effect is obtained can be selected. Particularly, it is contemplated that the weight ratio A):B) between the active compounds A) and B) may be situated between 50:1 and 1:50, more particularly between 20:1 and 1:20. Preferably said ratio A):B) is between 10:1 and 1:10, more preferably between 5:1 and 1:5.

These ratios are not intended to limit the nature of the invention and may provide a suitable means for tailoring the efficiency of broad classes of antimicrobial compositions which may require a combination of these active compounds A) and B).

In one embodiment, the invention relates to a method of controlling microbial growth on or in engineering material, which comprises applying an antimicrobially effective amount of an antimicrobial composition that comprises A) fludioxonil and at least one compound B) to the engineering material to be treated, wherein the active compounds A) and B) are present in a ratio A):B) by weight of from 5:1 to 1:5.

In addition to the aforementioned active compounds A) and B), the compositions according to the present invention optionally may further contain other active compounds C), e.g. other microbicides, in particular fungicides, and also insecticides. The following active compounds C) are mentioned as optional insecticides:

Phosphoric esters such as azinphos-ethyl, azinphos-methyl, 1-(4-chlorophenyl)-4-(O-ethyl,S-propyl)phosphoryloxypyrazole, chloropyrifos, coumaphos, demeton, demeton-S-methyl, diazinon, dichlorvos, dimethoate, ethoprophos, etrimfos, fenitrothion, fenthion, heptenophos, parathion, parathion-methyl, phosalone, phoxim, pirimiphos-ethyl, pirimiphos-methyl, profenofos, prothiofos, sulfprofos, triazophos and trichlorophon;

Carbamates such as aldicarb, bendiocarb, 2-(1-methylpropyl)-phenyl methylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb;

Organosilicon compounds, preferably dimethyl(phenyl)silylmethyl 3-phenoybenzyl ethers, such as dimethyl-(4-ethoxyhpenyl)silylmethyl 3-phenoxybenzyl ether or (dimethylphenyl)-silyl-methyl 2-phenoxy-6-pyridylmethyl ethers such as, for example, dimethyl(9-ethoxy-phenyl)silylmethyl 2-phenoxy-6-pyridylmethyl ether or [(phenyl)-3-(3-phenoxyphenyl)-propyl](dimethyl)-silanes, such as, for example, (4-ethoxyphenyl)-[3-(4-fluoro-3-phenoxy-phenyl-propyl] dimethyl silane.

Pyrethroids, such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoromethylvinyl)cyclopropane-carboxylate, fenpropathrin, fenfluthrin, fenvalerate, flucythrinate, flumethrin, fluvalinate, lambda cyhalothrin, gamma cyhalothrin, permethrin, resmethrin and tralomethrin;

Arylpyrazoles such as fipronil.

Nitroimines and nitromethylenes, such as imidacloprid, thiamethoxam, thiacloprid, acetamiprid and clothianidin.

The total amount of active substance A), or mixture of substances A), B) and optionally C) employed depends on the species and the occurrence of the microorganisms, the microbial count and the medium. The optimum dosage rate for use can be determined in each case by test series. In general, however, it suffices to employ 0.001 to 20% by weight, preferably 0.05 to 10% by weight, of the active compounds based on the material to be protected.

In one embodiment, the invention relates to a method of controlling microbial growth on or in engineering material, which comprises applying an antimicrobially effective amount of an antimicrobial composition that comprises A) fludioxonil, or mixtures thereof with at least one of the active compounds B), and optionally with at least one compound C), wherein the antimicrobial composition further comprises an insecticide C) selected from the group consisting of: imidacloprid, thiamethoxam and fipronil.

In another embodiment, the invention relates to a method of controlling microbial growth on or in engineering material, which comprises applying an antimicrobially effective amount of an antimicrobial composition that comprises A) fludioxonil, wherein B) is tebuconazole and the antimicrobial composition further comprises a carrier.

The active compound A), or mixtures thereof with at least one of the active compounds B), and optionally with at least one compound C), can be in the form of water-dilutable concentrations which are then applied in a customary manner in the form of a dilution with water, or in the form of so-called tank mixes which are prepared by concomitant dilution of the separately formulated components with water immediately prior to application. They can also be applied in the form of aqueous ready-for-use solutions or are used in unmodified form or together with adjuvants conventionally employed in the art of formulation. The formulations, i.e. the compositions, preparations or mixtures containing the active compounds and, where appropriate, a solid or liquid adjuvant, are prepared following art-known procedures, e.g. by homogeneously mixing and/or grinding the active compounds with extenders, e.g. solvents, solid carriers and, where appropriate, surface-active compounds (surfactants), to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomizing, dusting, scattering or pouring, brushing, dipping, soaking, impregnating or treating in closed pressure- or vacuum systems, are chosen in accordance with the intended objectives and the prevailing circumstances.

In one embodiment, the invention relates to a method of controlling microbial growth on or in engineering material, which comprises applying an antimicrobially effective amount of an antimicrobial composition that comprises A) fludioxonil, or mixtures thereof with at least one of the active compounds B), and optionally with at least one compound C), wherein said composition is applied to said material by a means selected from the group consisting of: spraying, atomizing, dusting, scattering, pouring, brushing, dipping, soaking, impregnating and treating in closed pressure- or vacuum systems.

For example, the active compound A), mixtures of A) and B), or microbicidal compositions or concentrates containing them can be used to inhibit the growth of microorganisms by introducing a microbicidally effective amount of the compositions onto, into, or at a locus of an engineering material or product subject to microbial attack. Suitable loci include, for example: cooling towers; air washers; boilers; mineral slurries; wastewater treatment; ornamental fountains; reverse osmosis filtration; ultrafiltration; ballast water; evaporative condensers; heat exchangers; plastics; emulsions; dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; detergents; industrial cleaners; floor polishes; laundry rinse water; metalworking fluids; conveyor lubricants; hydraulic fluids; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic food wrap; pools; and spas.

In another embodiment, the invention relates to an engineering material obtainable by a method as described above.

In yet another embodiment, the invention relates to an engineering material obtained by a method as described above.

In a further embodiment, the invention relates to an engineering material treated by a composition as described above.

In another embodiment, the invention relates to the use of an antimicrobial composition that comprises A) fludioxonil to control microbial growth on or in engineering material.

In another embodiment, the invention relates to the use of an antimicrobial composition that comprises A) fludioxonil to control microbial growth on or in engineering material, wherein said composition further comprises at least one compound B) selected from the group consisting of: azaconazole, bitertanol, bromuconazole, cyproconazole, diclobutrazol, difenoconazole, diniconazole, diniconazole-m, epoxiconazole, etaconazole, fenbuconazole, fluquinconazole, flusilazole, flutriafol, furconazole, furconazole-cis, hexaconazole, imibenconazole, ipconazole, metconazole, myclobutanil, oxpoconazole fumarate, paclobutrazol, pefurazoate, penconazole, propiconazole, prothioconazole, quinconazole, simeconazole, tebuconazole, tetraconazole, triadimefon, triadimenol, triticonazole, uniconazole, and uniconazole-p.

In one embodiment, the invention relates to an antimicrobial composition which comprises A) fludioxonil and at least one compound B1) selected from the group consisting of: azaconazole, bitertanol, bromuconazole, diclobutrazol, diniconazole, diniconazole-m, epoxiconazole, etaconazole, fenbuconazole, flusilazole, flutriafol, furconazole, furconazole-cis, hexaconazole, imibenconazole, ipconazole, metconazole, myclobutanil, oxpoconazole fumarate, paclobutrazol, pefurazoate, penconazole, propiconazole, quinconazole, simeconazole, tetraconazole, triadimefon, triadimenol, uniconazole, and uniconazole-p.

The ratio A):B1) between the active compounds A) and B1) in said compositions may vary within relatively broad ranges and will be dependent on the application aimed at as discussed above. Particularly, it is contemplated that the weight ratio A):B1) between the active compounds A) and B1) may be situated between 50:1 and 1:50, more particularly between 20:1 and 1:20. Preferably said ratio A):B1) is between 10:1 and 1:10, more preferably between 5:1 and 1:5.

In a further embodiment, the invention relates to an antimicrobial composition comprising the active compounds A) and B1), wherein the active compounds A) and B1) are present in a ratio A):B1) by weight of from 5:1 to 1:5.

In yet a further embodiment, the invention relates to an antimicrobial composition comprising the active compounds A) and B1), wherein B1) is propiconazole.

In addition to the aforementioned active compounds A) and B1), the compositions according to the present invention optionally may further contain other active compounds C), e.g. other microbicides, in particular fungicides, and also insecticides as discussed above. The active compounds C) mentioned above also are suitable for the present invention.

In another embodiment, the invention relates to an antimicrobial composition which comprises the active compounds A) and at least one compound B1), which further comprises an insecticide C) selected from the group consisting of: imidacloprid, thiamethoxam and fipronil.

Surprisingly, A) fludioxonil when used alone or in combination with at least one of the active compounds B1) displays a particularly powerful microbicidal activity against microorganisms which are relevant in the protection of industrial materials.

In one embodiment, the invention relates to a method of controlling microbial growth on or in industrial material, which comprises applying an antimicrobially effective amount of the antimicrobial composition comprising the active compounds A) and at least one compound B1) to the industrial material to be treated.

The term "industrial material" refers to natural substances of plant or animal origin such as leather or wood, or other non-live material of plant or animal origin subject to contamination by microorganisms. The term "industrial material" does not extend to plant propagation material such as seeds and plant cuttings.

Certain compositions containing the active compound A) and certain mixtures of the active compounds A) and B), or microbicidal compositions or concentrates containing them, are employed for protecting industrial materials that are natural substances of plant or animal origin such as leather, wood, wood products and derived timber products against microorganisms, for example against leather-destroying, leather-discolouring, wood-destroying or wood-discolouring fungi.

"Wood" is to be understood as meaning wood and wood products, for example, pulp and paper processing fluids; wet-lap ("wet-lap" refers to paper or other cellulosic product that is not completely dried after manufacture), derived timber products, lumber, plywood, chipboard, flakeboard, laminated beams, oriented strandboard, hardboard, and particleboard; paper food wrap, tropical wood, structural timber, wooden beams, railway sleepers, components of bridges, jetties, vehicles made of wood, boxes, pallets, containers, telegraph poles, wooden fences, wooden lagging, windows and doors made of wood, plywood, chipboard, joinery, or wooden products which are used, quite generally, for building houses or decks, in building joinery or wood products that are generally used in house-building, construction and carpentry.

The protection of wood is particularly effective when large-scale impregnating treatments, for example vacuum, double vacuum or pressure treatments, are used.

Microorganisms which can effect a degradation or change of the industrial materials which may be mentioned by way of example are bacteria, fungi, yeasts, algae and slime-forming organisms. The following groups of microorganisms may be mentioned by way of example, but without imposing any limitation: Wood-discolouring fungi—including *Ascomycetes; Ceratocystis* such as *Ceratocystis minor, Deuteromycetes; Aspergillus* such as *Aspergillus niger; Aureobasidium* such as *Aureobasidium pullulans; Dactylium* such as *Dactylium fusarioides; Penicillium* such as *Penicillium brevicaule, Penicillium variabile, Penicillium funiculosum, Penicillium citrinum* or *Penicillium pinophilum; Sclerophoma* such as *Sclerophoma pithyophila; Scopularia* such as *Scopularia phycomyces; Trichoderma* such as *Trichoderma viride, Trichoderma lignorum* or *Trichoderma virens; Zygomycetes; Mucor* such as *Mucor spinorus*. Wood-destroying fungi—

*Ascomycetes; Chaetomium* such as *Chaetomium globosum* or *Chaetomium alba-arenulum; Humicola* such as *Humicola grisea; Petriella* such as *Petriella setifera; Trichurus* such as *Trichurus spiralis; Basidiomycetes; Coniophora* such as *Coniophora puteana; Coriolus* such as *Coriolus versicolor; Donkioporia* such as *Donkioporia expaisa; Glenospora* such as *Glenospora graphii; Gloeophyllum* such as *Gloeophyllum abietinum* or *Gloeophyllum adoratum* or *Gl. protactum* or *Gloeophyllum sepiarium* or *Gl. trabeum; Lentinus* such as *Lentinus cyathiformes* or *Lentinus edodes* or *Lentinus lepideus* or *Lentinus grinus* or *L. squarrolosus; Oligoporus* such as *Oligoporus placenta; Paxillus* such as *Paxillus panuoides; Pleurotus* such as *Pleurotis ostreatus; Poria* such as *Poria monticola* or *Poria placenta* or *Poria vaillantii* or *Poria vaporaria; Serpula* such as *Serpula himantoides* or *Serpula lacrymans; Stereum* such as *Stereum hirsutum; Tyromyces* such as *Tyromyces palustris; Deuteromycetes; Alternaria* such as *Alternaria tenius, Alternaria alternata* or *Alternaria teniussima; Cladosporium* such as *Cladosporium herbarum* or *Cladosporium cladosporiodes; Stachybotrys* such as *Stachybotrys chartarum* (*Stachybotrys atra*).

In a further embodiment, the invention relates to a method of controlling microbial growth on or in industrial material, which comprises applying an antimicrobially effective amount of the antimicrobial composition comprising A) fludioxonil and at least one compound B1) to the industrial material to be treated, wherein the industrial material is selected from the group consisting of leather and wood.

In one embodiment, the invention relates to a method of controlling microbial growth on or in industrial material, which comprises applying an antimicrobially effective amount of the antimicrobial composition comprising A) fludioxonil and at least one compound B1) to the industrial material to be treated, wherein said composition is applied to said material by a means selected from the group cosisting of: spraying, atomizing, dusting, scattering, pouring, brushing, dipping, soaking, impregnating and treating in closed pressure- or vacuum systems.

In one embodiment, the invention relates to the use of an antimicrobial composition comprising A) fludioxonil and at least one compound B1) to control microbial growth on or in industrial material.

In a further embodiment, the invention relates to the use of an antimicrobial composition comprising A) fludioxonil and at least one compound B1) to control microbial growth on or in industrial material, wherein the industrial material is selected from the group consisting of: leather and wood.

In another embodiment, the invention relates to an industrial material obtainable by a method as described above.

In yet another embodiment, the invention relates to an industrial material obtained by a method as described above.

In a further embodiment, the invention relates to an industrial material treated by a composition as described above.

In another embodiment, the invention relates to an industrial material obtainable by a method as described above, wherein said material is selected from the group consisting of: leather and wood.

In yet another embodiment, the invention relates to an industrial material obtained by a method as described above, wherein said material is selected from the group consisting of: leather and wood.

In a further embodiment, the invention relates to an industrial material treated by a composition as described above, wherein said material is selected from the group consisting of: leather and wood.

In one embodiment, the invention relates to a method of preserving wood which comprises treating the wood with an antimicrobially effective amount of an antimicrobial composition consisting essentially of A) fludioxonil and a carrier.

In a further embodiment, the invention relates to a method of preserving wood which comprises treating the wood with an antimicrobially effective amount of an antimicrobial composition consisting essentially of A) fludioxonil and a carrier, wherein said composition is applied to said material by a means selected from the group cosisting of: spraying, atomizing, dusting, scattering, pouring, brushing, dipping, soaking, impregnating and treating in closed pressure- or vacuum systems.

In yet a further embodiment, the invention relates to the use of an antimicrobial composition consisting essentially of: A) fludioxonil and a carrier to control microbial growth on or in wood.

In another embodiment, the invention relates to wood obtainable by a method as described above.

In yet another embodiment, the invention relates to wood obtained by a method as described above.

In a further embodiment, the invention relates to wood treated by a composition as described above.

In one embodiment, the invention relates to a method of controlling microbial growth on or in industrial material, which comprises applying an antimicrobially effective amount of an antimicrobial composition comprising A) fludioxonil and at least one compound B2) selected from the group consisting of: cyproconazole, propiconazole, triticonazole and fluquinconazole to the industrial material to be treated. In particular, the invention relates to a method of controlling microbial growth on or in industrial materials, which comprises applying an antimicrobially effective amount of an antimicrobial composition comprising A) fludioxonil and at least one compound B2) selected from propiconazole and fluquinconazole to the industrial material to be treated.

The ratio A):B2) between the active compounds A) and B2) in said compositions may vary within relatively broad ranges and will be dependent on the application aimed at as discussed above. Particularly, it is contemplated that the weight ratio A):B2) between the active compounds A) and B2) may be situated between 50:1 and 1:50, more particularly between 20:1 and 1:20. Preferably said ratio A):B2) is between 10:1 and 1:10, more preferably between 5:1 and 1:5.

In a further embodiment, the invention relates to a method of controlling microbial growth on or in industrial material, which comprises applying an antimicrobially effective amount of an antimicrobial composition comprising A) fludioxonil and at least one compound B2) to the industrial material to be treated, wherein the active compounds A) fludioxonil and B2) are present in a ratio A):B2) by weight of from 5:1 to 1:5.

In addition to the aforementioned active compounds A) and B2), the compositions according to the present invention optionally may further contain other active compounds C), e.g. other microbicides, in particular fungicides, and also insecticides as discussed above. The active compounds C) mentioned above also are suitable for the present invention.

In yet a further embodiment, the invention relates to a method of controlling microbial growth on or in industrial material, which comprises applying an antimicrobially effective amount of an antimicrobial composition comprising A) fludioxonil and at least one compound B2) to the industrial material to be treated, wherein the antimicrobial composition further comprises an insecticide C) selected from the group consisting of: imidacloprid, thiamethoxam and fipronil.

In yet a further embodiment, the invention relates to a method of controlling microbial growth on or in industrial material, which comprises applying an antimicrobially effective amount of an antimicrobial composition comprising A) fludioxonil and at least one compound B2) to the industrial material to be treated, wherein B2) is selected from the group consisting of: propiconazole and cyproconazole.

In a further embodiment, the invention relates to a method of controlling microbial growth on or in industrial materials, which comprises applying an antimicrobially effective amount of an antimicrobial composition comprising A) fludioxonil and at least one compound B2) to the industrial material to be treated, wherein the industrial material is selected from the group consisting of: leather and wood.

In yet a further embodiment, the invention relates to a method of controlling microbial growth on or in industrial materials, which comprises applying an antimicrobially effective amount of an antimicrobial composition comprising A) fludioxonil and at least one compound B2) to the industrial material to be treated, wherein said composition is applied to said material by a means selected from the group cosisting of: spraying, atomizing, dusting, scattering, pouring, brushing, dipping, soaking, impregnating and treating in closed pressure- or vacuum systems.

In another embodiment, the invention relates to an industrial material obtainable by a method as described above.

In yet another embodiment, the invention relates to an industrial material obtained by a method as described above.

In a further embodiment, the invention relates to an industrial material treated by a composition as described above.

In another embodiment, the invention relates to an industrial material obtainable by a method as described above, wherein said material is selected from the group consisting of: leather and wood.

In yet another embodiment, the invention relates to an industrial material obtained by a method as described above, wherein said material is selected from the group consisting of: leather and wood.

In a further embodiment, the invention relates to an industrial material treated by a composition as described above, wherein said material is selected from the group consisting of: leather and wood.

In a further embodiment, the invention relates to the use of an antimicrobial composition that comprises A) fludioxonil and at least one compound B2) selected from the group consisting of: cyproconazole, propiconazole, triticonazole and fluquinconazole to control microbial growth on or in industrial material.

In yet a further embodiment, the invention relates to the use of an antimicrobial composition that comprises A) fludioxonil and at least one compound B2) selected from the group consisting of: cyproconazole, propiconazole, triticonazole and fluquinconazole to control microbial growth on or in industrial material, wherein the industrial material is selected from the group consisting of: leather and wood.

Compositions of A) fludioxonil and compound B2) selected from cyproconazole and propiconazole are particularly suitable for use in the protection of wood or wood products. In particular, compositions of A) fludioxonil and propiconazole for use in the protection of wood or wood products are preferred.

For example, in order to protect a locus such as wood from decay it can treated with the active compound A), or mixtures thereof with at least one of the active compounds B) in compositions according to the present invention. Such treatment is applied by several different procedures such as, for example, by treating the wood in closed pressure- or vacuum systems, in thermal- or dip systems and the like, or by a wide variety of surface treatments, e.g. by brushing, dipping, spraying or soaking the wood with a formulation containing the wood-preserving agents A) and B).

Those skilled in the art will recognize that mixtures or combinations of the active compound A) with at least one of the active compounds B) of the present invention may be added to a locus sequentially, simultaneously, or may be combined before being added to the locus. Sequential applications include so-called split applications where the active compounds are applied up to a few days one after the other.

The abovementioned formulations and compositions can be prepared in a manner known per se, for example by mixing the active compound(s) with a suitable carrier such as at least one solvent or diluent, emulsifier, dispersant and/or binder or fixative, water repellant, optionally siccatives, antifreeze agents, antifoams and UV stabilisers, and optionally colourants and pigments as well as other processing auxiliaries.

Suitable solvents or diluents are organochemical solvents or solvent mixtures and/or a polar organic solvent or solvent mixture and/or an oily or oil-type organochemical solvent or solvent mixture and/or water, if appropriate together with an emulsifier and/or wetting composition. Customary water-insoluble oily or oil-type solvents of low volatility which are preferably used are the vegetable oils, methylated vegetable oils, particular mineral oils/mineral-oil-containing solvent mixtures or their aromatic fractions. White spirit, petroleum or alkylbenzenes, and additionally spindle oil and monochloronaphthalene may be mentioned as being preferred. The boiling ranges of these solvent (mixtures) of low volatility cover a range of approximately 170° C. to not more than 350° C.

The above-described oily or oil-type solvents of low volatility can be replaced partially by more volatile organochemical solvents.

To prepare a wood preservative, some of the above described solvent or solvent mixture is preferably replaced by a polar organochemical solvent or solvent mixture. Solvents which are preferably used are those containing hydroxyl groups, ester groups, ether groups or mixtures of this functionality. Examples which may be mentioned are esters or glycol ethers. Binders are to be understood according to the invention as being synthetic resins, binding drying oils, for example based on acrylic resins, vinyl resins, polyester resins, polyurethane resins, alkyd resins, phenol resins, hydrocarbon resins or silicone resins which can be diluted with water or are soluble, dispersible or emulsifiable in organochemical solvents. The binder used can be employed as a solution, emulsion or dispersion. Mixtures of alkyd resins and drying vegetable oil are preferably used. Alkyd resins with an oil content of between 45 and 70% are particularly preferred.

All or some of the abovementioned binder can be replaced by a fixative (mixture) or a plasticiser (mixture). These additives are intended to prevent volatilization of the active compound as well as crystallisation or precipitation. They preferably replace 0.01 to 30% of the binder (based on 100% of the binder used).

The plasticisers are from the chemical classes of the phthalic esters such as dibutyl, dioctyl or benzyl butyl phthalate, phosphoric esters such as tributyl phosphate, adipic esters such as di-(2-ethylhexyl) adipate, stearates such as butyl stearate and amyl stearate, oleates such as butyl oleate, glycerol ethers or higher-molecular-weight glycol ethers, glycerol esters as well as p-toluenesulphonic esters.

Fixatives are based, from the chemical point of view, on polyvinyl alkyl ethers such as, for example, polyvinyl methyl ether, or ketones such as benzophenone or ethylenebenzophenone.

The preferred solvent or diluent is water, if appropriate in a mixture with one or more of the abovementioned solvents or diluents, emulsifiers and dispersants.

FORMULATION EXAMPLES

In the examples which follow (%=percent by weight). The examples are intended to illustrate and not limit the invention, "active compound(s)" being understood as meaning A) fludioxonil or a mixture of A) fludioxonil with the at least one of active compound B) in a mixing ratio A):B) of from 5:1 to 1:5.

EXAMPLE F1

| Emulsifiable concentrates | | | |
|---|---|---|---|
| | a) | b) | c) |
| Active Compound(s) | 25% | 40% | 50% |
| calcium dodecylbenzenesulfonate | 5% | 8% | 6% |
| castor oil polyethylene glycol ether | 5% | — | — |
| tributylphenol polyethylene glycol ether | — | 12% | 4% |
| Cyclohexanone | — | 15% | 20% |
| xylene mixture | 65% | 25% | 20% |

Emulsions of any desired concentration can be prepared from this concentrate by dilution with water, and can be employed in materials protection applications.

EXAMPLE F2

| Dusts | | |
|---|---|---|
| | a) | b) |
| Active Compound(s) | 5% | 8% |
| Talc | 95% | — |
| Kaolin | — | 92% |

Ready-to-use dusts are obtained by mixing the active ingredients with the carrier and grinding the mixture in a suitable mill.

EXAMPLE F3

| Wettable powders | | | |
|---|---|---|---|
| | a) | b) | c) |
| Active Compound(s) | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether | — | 2% | — |
| highly dispersed silicic acid | 5% | 10% | 10% |
| Kaolin | 62% | 27% | — |

The active ingredient is mixed thoroughly with the additives and the mixture is ground thoroughly in a suitable mill affording wettable powders which can be diluted with water to give suspensions of any desired concentration.

EXAMPLE F4

| Suspoemulsions | |
|---|---|
| | a) |
| Active Compound(s) | 22.5% |
| sulfated nonylphenol (polyoxyethylene condensate) | 0.1% |
| phosphated tristyrylphenol (polyoxyethylene condensate) | 4% |
| sodium lignosulfonate (polyoxyethylene condensate) | 2% |

EXAMPLE F4-continued

| Suspoemulsions | |
|---|---|
| | a) |
| NaOH (50%) | 0.1% |
| silicone defoaming agent | 0.1% |
| Glycerin | 20% |
| xanthan gum | 0.2% |
| Water | 51% |

This formulation is suitable for mixtures of solid and liquid active ingredients. The solid active ingredient(s) are mixed thoroughly with a portion of the emulsifiers and water and the mixture is ground thoroughly in a suitable mill. Another portion of the emulsifiers and water are mixed with the liquid active ingredient(s). The two mixtures are combined along with any other inert ingredients (such as thickeners, etc.) that are to be used in the formulation.

It is to be understood that changes and variations may be made without departing from the spirit and scope of the invention as defined by the appended claims.

The invention claimed is:

1. An antimicrobial composition comprising an antimicrobially effective amount of A) fludioxonil and B) propiconazole, said antimicrobially effective amount of A) fludioxonil and B) propiconazole providing a synergistic effect.

2. An antimicrobial composition according to claim 1, wherein the active compounds A) and B) are present in a ratio A):B) by weight of from 5:1 to 1:5.

3. An antimicrobial composition according to claim 1, which further comprises an insecticide C) selected from the group consisting of: imidacloprid, thiamethoxam and fipronil.

4. A method of controlling microbial growth on or in industrial material, which comprises applying an antimicrobially effective amount of the antimicrobial composition according to claim 1 to the industrial material to be treated.

5. A method according to claim 4, wherein the industrial material is selected from the group consisting of: leather and wood.

6. A method according to claim 4, wherein said composition is applied to said material by a means selected from the group consisting of: spraying, atomizing, dusting, scattering, pouring, brushing, dipping, soaking, impregnating and treating in closed pressure- or vacuum systems.

7. Industrial material obtained by the method of claim 4.

8. Industrial material according to claim 7, wherein said material is selected from the group consisting of: leather and wood.

9. An antimicrobial composition according to claim 1, wherein the antimicrobial composition comprises a solution, a suspension, or a microemulsion, and the fludioxonil and propiconazole together represent from about 0.2 to about 15 percent by weight of the solution, suspension, or microemulsion.

10. An antimicrobial composition according to claim 1, wherein the antimicrobial composition comprises a water-dilutable concentrate.

11. An antimicrobial composition according to claim 1, wherein the antimicrobial composition comprises an aqueous ready-for-use solution.

12. An antimicrobial composition according to claim 1, wherein the antimicrobial composition further comprises at least composition component selected from a solid adjuvant, a liquid adjuvant, a solvent, a surfactant, a water repellent, an antifreeze agent, an antifoam, and a UV stabilizer.

13. An antimicrobial composition according to claim 1, wherein the antimicrobial composition further comprises at least one solvent selected from vegetable oil, methylated vegetable oil, mineral oil, white spirit oil, petroleum oil, alkylbenzene, spindle oil, and monochloronaphthalene.

14. An antimicrobial composition according to claim 1, wherein the antimicrobial composition further comprises at least one solvent selected from a solvent containing a hydroxyl group, a solvent containing an ester group, a solvent containing an ether group, or a solvent containing a combination of a hydroxyl group, an ester group, and an ether group.

15. An antimicrobial composition according to claim 1, wherein the antimicrobial composition further comprises at least one solvent selected from an ester or a glycol ether.

16. A synergistic antimicrobial composition comprising A) fludioxonil and B) propiconazole.

17. A synergistic antimicrobial composition according to claim 16, wherein the antimicrobial composition comprises a solution, a suspension, or a microemulsion, and the fludioxonil and propiconazole together represent from about 0.2 to about 15 percent by weight of the solution, suspension, or microemulsion.

18. A composition for impregnating industrial materials comprising A) fludioxonil and B) propiconazole.

19. A composition according to 18, wherein the industrial materials are leather, wood, wood products and derived timber products.

20. A composition according to claim 19, wherein the composition comprises a solution, a suspension, or a microemulsion, and the fludioxonil and propiconazole together represent from about 0.2 to about 15 percent by weight of the solution, suspension, or microemulsion.

* * * * *